(12) United States Patent
Jackson

(10) Patent No.: US 8,105,368 B2
(45) Date of Patent: Jan. 31, 2012

(54) DYNAMIC STABILIZATION CONNECTING MEMBER WITH SLITTED CORE AND OUTER SLEEVE

(76) Inventor: Roger P. Jackson, Prairie Village, KS (US)

( * ) Notice: Subject to any disclaimer, the term of this patent is extended or adjusted under 35 U.S.C. 154(b) by 752 days.

(21) Appl. No.: 11/888,612

(22) Filed: Aug. 1, 2007

(65) Prior Publication Data
US 2007/0270860 A1 Nov. 22, 2007

Related U.S. Application Data

(63) Continuation-in-part of application No. 11/522,503, filed on Sep. 14, 2006.

(60) Provisional application No. 60/850,464, filed on Oct. 10, 2006, provisional application No. 60/722,300, filed on Sep. 30, 2005, provisional application No. 60/725,445, filed on Oct. 11, 2005, provisional application No. 60/728,912, filed on Oct. 21, 2005, provisional application No. 60/736,112, filed on Nov. 10, 2005, provisional application No. 60/832,644, filed on Jul. 21, 2006.

(51) Int. Cl.
*A61B 17/56* (2006.01)
(52) U.S. Cl. ..................................... 606/326
(58) Field of Classification Search .............. 606/326, 606/246, 254, 264, 301, 257, 278, 250, 251, 606/253
See application file for complete search history.

(56) References Cited

U.S. PATENT DOCUMENTS

| | | |
|---|---|---|
| 854,956 A | 5/1907 | Martin |
| 2,243,717 A | 5/1941 | Moreira |
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |
| 4,190,091 A | 2/1980 | Colognori |
| 4,373,754 A | 2/1983 | Bollfrass et al. |
| 4,448,191 A | 5/1984 | Rodnyansky et al. |
| 4,484,570 A | 11/1984 | Sutter et al. |

(Continued)

FOREIGN PATENT DOCUMENTS

CA 2577436 6/2006

(Continued)

OTHER PUBLICATIONS

*EBI Omega 21* Brochure, EBI Spine Systems, pub. 1999.

(Continued)

*Primary Examiner* — Pedro Philogene
(74) *Attorney, Agent, or Firm* — John C. McMahon

(57) ABSTRACT

A dynamic fixation medical implant having at least two bone anchors includes a longitudinal connecting member assembly having an elongate core and an outer sleeve. The core may be substantially cylindrical, of one-piece construction, and includes end portions for attachment to the bone anchors. A portion of the core extending between the bone anchors has at least one slit. The outer sleeve may include compression grooves. The sleeve surrounds the core and extends between the pair of bone anchors, the sleeve being compressible in a longitudinal direction between the bone anchors.

16 Claims, 5 Drawing Sheets

U.S. PATENT DOCUMENTS

| | | |
|---|---|---|
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Barker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |

| | | | |
|---|---|---|---|
| 6,117,137 A | 9/2000 | Halm et al. | |
| 6,132,431 A | 10/2000 | Nilsson et al. | |
| 6,132,432 A | 10/2000 | Richelsoph | |
| 6,132,434 A | 10/2000 | Sherman et al. | |
| 6,136,002 A | 10/2000 | Shih et al. | |
| 6,139,549 A | 10/2000 | Keller | |
| 6,143,032 A | 11/2000 | Schafer et al. | |
| 6,146,383 A | 11/2000 | Studer et al. | |
| 6,183,472 B1 | 2/2001 | Lutz | |
| 6,186,718 B1 | 2/2001 | Fogard | |
| 6,187,005 B1 | 2/2001 | Brace et al. | |
| 6,193,720 B1 | 2/2001 | Yuan et al. | |
| 6,214,012 B1 | 4/2001 | Karpman et al. | |
| RE37,161 E | 5/2001 | Michelson et al. | |
| 6,224,596 B1 | 5/2001 | Jackson | |
| 6,224,598 B1 | 5/2001 | Jackson | |
| 6,235,028 B1 | 5/2001 | Brumfield et al. | |
| 6,235,034 B1 | 5/2001 | Bray | |
| 6,241,730 B1 | 6/2001 | Alby | |
| 6,248,105 B1 | 6/2001 | Schlapfer et al. | |
| 6,248,107 B1 | 6/2001 | Foley et al. | |
| 6,251,112 B1 | 6/2001 | Jackson | |
| 6,254,146 B1 | 7/2001 | Church | |
| 6,254,602 B1 | 7/2001 | Justis | |
| 6,267,764 B1 | 7/2001 | Elberg | |
| 6,267,765 B1 | 7/2001 | Taylor et al. | |
| 6,273,888 B1 | 8/2001 | Justis | |
| 6,277,122 B1 | 8/2001 | McGahan et al. | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,302,888 B1 | 10/2001 | Mellinger et al. | |
| 6,309,391 B1 | 10/2001 | Crandall et al. | |
| 6,315,564 B1 | 11/2001 | Levisman | |
| 6,315,779 B1 | 11/2001 | Morrison et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,402,752 B2 | 6/2002 | Schaffler-Wachter et al. | |
| 6,402,757 B1 | 6/2002 | Moore et al. | |
| 6,440,133 B1 | 8/2002 | Beale et al. | |
| 6,440,137 B1 | 8/2002 | Horvath et al. | |
| 6,443,956 B1 | 9/2002 | Ray | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,478,801 B1 | 11/2002 | Ralph et al. | |
| 6,485,491 B1 | 11/2002 | Farris et al. | |
| 6,485,492 B1 | 11/2002 | Halm et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,511,484 B2 | 1/2003 | Torode et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,539,826 B2 | 4/2003 | Oesterle et al. | |
| 6,540,749 B2 | 4/2003 | Schafer et al. | |
| 6,547,790 B2 | 4/2003 | Harkey, III et al. | |
| 6,551,320 B2 | 4/2003 | Liebermann | |
| 6,551,323 B2 | 4/2003 | Doubler et al. | |
| 6,554,831 B1 | 4/2003 | Rivard et al. | |
| 6,554,832 B2 | 4/2003 | Shluzas | |
| 6,554,834 B1 | 4/2003 | Crozet et al. | |
| 6,558,387 B2 | 5/2003 | Errico et al. | |
| 6,562,038 B1 | 5/2003 | Morrison | |
| 6,562,040 B1 | 5/2003 | Wagner | |
| 6,565,565 B1 | 5/2003 | Yuan et al. | |
| 6,565,567 B1 | 5/2003 | Haider | |
| 6,572,618 B1 | 6/2003 | Morrison | |
| 6,582,436 B2 | 6/2003 | Schlapfer et al. | |
| 6,582,466 B1 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,599,294 B2 | 7/2003 | Fuss et al. | |
| 6,610,063 B2 | 8/2003 | Kumar et al. | |
| 6,613,050 B1 | 9/2003 | Wagner et al. | |
| 6,616,667 B1 | 9/2003 | Steiger et al. | |
| 6,616,669 B2 | 9/2003 | Ogilvie | |
| 6,623,485 B2 | 9/2003 | Doubler et al. | |
| 6,626,347 B2 | 9/2003 | Ng | |
| 6,626,907 B2 | 9/2003 | Campbell et al. | |
| 6,626,908 B2 | 9/2003 | Cooper et al. | |
| 6,635,059 B2 | 10/2003 | Randall et al. | |
| 6,635,060 B2 | 10/2003 | Hanson et al. | |
| 6,648,885 B1 | 11/2003 | Friesem | |
| 6,648,887 B2 | 11/2003 | Ashman | |
| 6,648,888 B1 | 11/2003 | Shluzas | |
| 6,652,526 B1 | 11/2003 | Arafiles | |
| 6,652,765 B1 | 11/2003 | Beaty | |
| 6,656,179 B1 | 12/2003 | Schaefer et al. | |
| 6,656,181 B2 | 12/2003 | Dixon et al. | |
| 6,660,004 B2 | 12/2003 | Barker et al. | |
| 6,660,006 B2 | 12/2003 | Markworth et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Benlloch et al. | |
| 6,679,833 B2 | 1/2004 | Smith et al. | |
| 6,682,529 B2 | 1/2004 | Stahurski | |
| 6,682,530 B2 | 1/2004 | Dixon et al. | |
| 6,689,133 B2 | 2/2004 | Morrison et al. | |
| 6,689,134 B2 | 2/2004 | Ralph et al. | |
| 6,695,843 B2 | 2/2004 | Biedermann et al. | |
| 6,695,851 B2 | 2/2004 | Zdeblick et al. | |
| 6,699,249 B2 | 3/2004 | Schlapfer et al. | |
| 6,706,045 B2 | 3/2004 | Lin et al. | |
| 6,712,818 B1 | 3/2004 | Michelson | |
| 6,716,213 B2 | 4/2004 | Shitoto | |
| 6,716,214 B1 | 4/2004 | Jackson | |
| 6,716,247 B2 | 4/2004 | Michelson | |
| 6,723,100 B2 | 4/2004 | Biedermann et al. | |
| 6,730,093 B2 | 5/2004 | Saint Martin | |
| 6,730,127 B2 | 5/2004 | Michelson | |
| 6,733,502 B2 | 5/2004 | Altarac et al. | |
| 6,736,816 B2 | 5/2004 | Ritland | |
| 6,736,820 B2 | 5/2004 | Biedermann et al. | |
| 6,740,086 B2 | 5/2004 | Richelsoph | |
| 6,743,231 B1 | 6/2004 | Gray et al. | |
| 6,746,449 B2 | 6/2004 | Jones et al. | |
| 6,755,829 B1 | 6/2004 | Bono et al. | |
| 6,755,835 B2 | 6/2004 | Schultheiss et al. | |
| 6,755,836 B1 | 6/2004 | Lewis | |
| 6,761,723 B2 | 7/2004 | Butterman et al. | |
| 6,767,351 B2 | 7/2004 | Orbay et al. | |
| 6,770,075 B2 | 8/2004 | Howland | |
| 6,778,861 B1 | 8/2004 | Liebrecht et al. | |
| 6,780,186 B2 | 8/2004 | Errico et al. | |
| 6,783,527 B2 | 8/2004 | Drewry et al. | |
| 6,790,209 B2 | 9/2004 | Beale et al. | |
| 6,802,844 B2 | 10/2004 | Ferree | |
| 6,827,719 B2 | 12/2004 | Ralph et al. | |
| 6,830,571 B2 | 12/2004 | Lenke et al. | |
| 6,835,196 B2 | 12/2004 | Biedermann et al. | |
| 6,837,889 B2 | 1/2005 | Shluzas | |
| 6,840,940 B2 | 1/2005 | Ralph et al. | |
| 6,843,791 B2 | 1/2005 | Serhan | |
| 6,857,343 B1 | 2/2005 | Easterbrooks et al. | |
| 6,858,031 B2 | 2/2005 | Morrison et al. | |
| 6,869,432 B2 | 3/2005 | Schlapfer et al. | |
| 6,869,433 B2 | 3/2005 | Glascott | |
| 6,872,208 B1 | 3/2005 | McBride et al. | |
| 6,896,676 B2 | 5/2005 | Zubok et al. | |
| 6,896,677 B1 | 5/2005 | Lin | |
| 6,932,817 B2 | 8/2005 | Baynham et al. | |
| 6,932,820 B2 | 8/2005 | Osman | |
| 6,945,972 B2 | 9/2005 | Frigg et al. | |
| 6,953,462 B2 | 10/2005 | Liebermann | |
| 6,955,677 B2 | 10/2005 | Dahners | |
| 6,958,065 B2 | 10/2005 | Ueyama et al. | |

| | | | | | | |
|---|---|---|---|---|---|---|
| 6,964,664 B2 | 11/2005 | Freid et al. | | 7,563,283 B2 | 7/2009 | Kwak |
| 6,964,665 B2 | 11/2005 | Thomas et al. | | 7,588,589 B2 | 9/2009 | Falahee |
| 6,964,667 B2 | 11/2005 | Shaolian et al. | | 7,601,166 B2 | 10/2009 | Biedermann et al. |
| 6,966,910 B2 | 11/2005 | Ritland | | 7,604,653 B2 | 10/2009 | Kitchen |
| 6,974,460 B2 | 12/2005 | Carbone et al. | | 7,604,654 B2 | 10/2009 | Fallin et al. |
| 6,979,334 B2 | 12/2005 | Dalton | | 7,611,518 B2 | 11/2009 | Walder et al. |
| 6,981,973 B2 | 1/2006 | McKinley | | 7,615,068 B2 | 11/2009 | Timm et al. |
| 6,986,771 B2 | 1/2006 | Paul et al. | | 7,621,912 B2 * | 11/2009 | Harms et al. .................... 606/59 |
| 6,989,011 B2 * | 1/2006 | Paul et al. .................... 606/250 | | 7,621,940 B2 * | 11/2009 | Harms et al. .................... 606/257 |
| 6,989,044 B2 * | 1/2006 | Zhang et al. .................... 95/90 | | 7,625,393 B2 | 12/2009 | Fallin et al. |
| 6,991,632 B2 | 1/2006 | Ritland | | 7,632,292 B2 | 12/2009 | Sengupta et al. |
| 7,004,947 B2 | 2/2006 | Shluzas et al. | | 7,641,673 B2 | 1/2010 | Le Couedic et al. |
| RE39,035 E | 3/2006 | Finn et al. | | 7,651,515 B2 * | 1/2010 | Mack et al. .................... 606/254 |
| 7,008,422 B2 | 3/2006 | Foley et al. | | 7,655,026 B2 | 2/2010 | Justis et al. |
| 7,008,424 B2 | 3/2006 | Teitelbaum | | 7,658,739 B2 | 2/2010 | Shluzas |
| 7,011,660 B2 | 3/2006 | Sherman et al. | | 7,658,752 B2 | 2/2010 | Labrom et al. |
| 7,018,378 B2 | 3/2006 | Biedermann et al. | | 7,682,375 B2 | 3/2010 | Ritland |
| 7,018,379 B2 | 3/2006 | Drewry et al. | | 7,695,496 B2 | 4/2010 | Labrom et al. |
| 7,022,122 B2 | 4/2006 | Amrein et al. | | 7,695,498 B2 | 4/2010 | Ritland |
| 7,029,475 B2 | 4/2006 | Panjabi | | 7,695,514 B2 | 4/2010 | Kwak |
| RE39,089 E | 5/2006 | Ralph et al. | | 2001/0001119 A1 | 5/2001 | Lombardo |
| 7,052,497 B2 | 5/2006 | Sherman et al. | | 2001/0010000 A1 | 7/2001 | Gertzbein |
| 7,056,321 B2 | 6/2006 | Pagliuca et al. | | 2001/0023350 A1 | 9/2001 | Choi |
| 7,066,062 B2 | 6/2006 | Flesher | | 2001/0029375 A1 | 10/2001 | Betz |
| 7,066,937 B2 | 6/2006 | Shluzas | | 2001/0037111 A1 | 11/2001 | Dixon et al. |
| 7,081,116 B1 | 7/2006 | Carly | | 2002/0007184 A1 | 1/2002 | Ogilvie et al. |
| 7,083,621 B2 | 8/2006 | Shaolian et al. | | 2002/0013586 A1 | 1/2002 | Justis et al. |
| 7,087,057 B2 | 8/2006 | Konieczynski et al. | | 2002/0035366 A1 | 3/2002 | Walder et al. |
| 7,090,674 B2 | 8/2006 | Doubler et al. | | 2002/0045898 A1 | 4/2002 | Freid et al. |
| 7,090,679 B2 | 8/2006 | Saint-Martin et al. | | 2002/0058942 A1 | 5/2002 | Biedermann et al. |
| 7,090,680 B2 | 8/2006 | Bonati et al. | | 2002/0068975 A1 | 6/2002 | Teitelbaum et al. |
| 7,094,242 B2 | 8/2006 | Ralph et al. | | 2002/0072751 A1 | 6/2002 | Jackson |
| 7,118,576 B2 | 10/2006 | Gitis et al. | | 2002/0077701 A1 | 6/2002 | Kuslich |
| 7,121,755 B2 | 10/2006 | Schlapfer et al. | | 2002/0082602 A1 | 6/2002 | Biedermann et al. |
| 7,125,410 B2 | 10/2006 | Freudiger | | 2002/0095153 A1 | 7/2002 | Jones et al. |
| 7,125,426 B2 | 10/2006 | Moumene et al. | | 2002/0111626 A1 | 8/2002 | Ralph et al. |
| 7,128,743 B2 | 10/2006 | Metz-Stavenhagen | | 2002/0133159 A1 | 9/2002 | Jackson |
| 7,137,985 B2 | 11/2006 | Jahng | | 2002/0143341 A1 | 10/2002 | Biedermann et al. |
| 7,141,051 B2 | 11/2006 | Janowski et al. | | 2002/0173789 A1 | 11/2002 | Howland |
| 7,144,396 B2 | 12/2006 | Shluzas | | 2002/0193795 A1 | 12/2002 | Gertzbein et al. |
| 7,163,538 B2 | 1/2007 | Altarac et al. | | 2003/0023240 A1 | 1/2003 | Amrein et al. |
| 7,163,539 B2 | 1/2007 | Abdelgany et al. | | 2003/0023243 A1 | 1/2003 | Biedermann et al. |
| 7,166,108 B2 | 1/2007 | Mazda et al. | | 2003/0073996 A1 | 4/2003 | Doubler et al. |
| 7,179,261 B2 | 2/2007 | Sicvol et al. | | 2003/0083657 A1 | 5/2003 | Drewry et al. |
| 7,186,255 B2 | 3/2007 | Baynham et al. | | 2003/0093078 A1 | 5/2003 | Ritland |
| 7,188,626 B2 | 3/2007 | Foley et al. | | 2003/0100896 A1 | 5/2003 | Biedermann et al. |
| 7,207,991 B2 | 4/2007 | Michelson | | 2003/0105460 A1 | 6/2003 | Crandall et al. |
| 7,207,992 B2 | 4/2007 | Ritland | | 2003/0109880 A1 | 6/2003 | Shirado et al. |
| 7,211,085 B2 | 5/2007 | Michelson | | 2003/0114852 A1 | 6/2003 | Biedermann et al. |
| 7,211,086 B2 | 5/2007 | Biedermann et al. | | 2003/0125741 A1 | 7/2003 | Biedermann et al. |
| 7,211,087 B2 | 5/2007 | Young | | 2003/0149432 A1 | 8/2003 | Frigg et al. |
| 7,214,227 B2 | 5/2007 | Colleran et al. | | 2003/0153911 A1 | 8/2003 | Shluzas |
| 7,223,268 B2 | 5/2007 | Biedermann | | 2003/0163133 A1 | 8/2003 | Altarac et al. |
| 7,229,441 B2 | 6/2007 | Trieu et al. | | 2003/0171749 A1 | 9/2003 | Le Couedic et al. |
| 7,264,621 B2 | 9/2007 | Coates et al. | | 2003/0176862 A1 | 9/2003 | Taylor et al. |
| 7,270,665 B2 | 9/2007 | Morrison et al. | | 2003/0191470 A1 | 10/2003 | Ritland |
| 7,282,064 B2 | 10/2007 | Chin | | 2003/0199873 A1 | 10/2003 | Richelsoph |
| 7,291,151 B2 | 11/2007 | Alvarez | | 2003/0208203 A1 | 11/2003 | Lim et al. |
| 7,291,153 B2 | 11/2007 | Glascott | | 2003/0208204 A1 | 11/2003 | Bailey et al. |
| 7,294,128 B2 | 11/2007 | Alleyne et al. | | 2003/0212398 A1 | 11/2003 | Jackson |
| 7,294,129 B2 | 11/2007 | Hawkins et al. | | 2003/0216735 A1 | 11/2003 | Altarac et al. |
| 7,306,603 B2 | 12/2007 | Boehm, Jr. et al. | | 2003/0220642 A1 | 11/2003 | Freudiger |
| 7,306,604 B2 | 12/2007 | Carli | | 2003/0220643 A1 | 11/2003 | Ferree |
| 7,306,606 B2 | 12/2007 | Sasing | | 2003/0225408 A1 | 12/2003 | Nichols et al. |
| 7,314,467 B2 | 1/2008 | Howland | | 2004/0002708 A1 | 1/2004 | Ritland |
| 7,316,684 B1 | 1/2008 | Baccelli et al. | | 2004/0006342 A1 | 1/2004 | Altarac et al. |
| 7,322,979 B2 | 1/2008 | Crandall et al. | | 2004/0049189 A1 | 3/2004 | Le Couedic et al. |
| 7,329,258 B2 | 2/2008 | Studer | | 2004/0049190 A1 | 3/2004 | Biedermann et al. |
| 7,335,201 B2 | 2/2008 | Doubler et al. | | 2004/0073215 A1 | 4/2004 | Carli |
| 7,335,202 B2 | 2/2008 | Matthis et al. | | 2004/0078082 A1 | 4/2004 | Lange |
| 7,338,490 B2 | 3/2008 | Ogilvie et al. | | 2004/0087949 A1 | 5/2004 | Bono et al. |
| 7,338,491 B2 | 3/2008 | Baker et al. | | 2004/0087952 A1 | 5/2004 | Borgstrom et al. |
| 7,361,196 B2 | 4/2008 | Fallin et al. | | 2004/0092934 A1 | 5/2004 | Howland |
| 7,377,921 B2 | 5/2008 | Studer et al. | | 2004/0097933 A1 | 5/2004 | Lourdel et al. |
| 7,476,238 B2 | 1/2009 | Panjabi | | 2004/0116929 A1 | 6/2004 | Barker et al. |
| 7,491,208 B2 | 2/2009 | Pond, Jr. et al. | | 2004/0138662 A1 | 7/2004 | Landry et al. |
| 7,556,639 B2 | 7/2009 | Rothman et al. | | 2004/0143265 A1 | 7/2004 | Landry et al. |
| 7,559,942 B2 | 7/2009 | Paul et al. | | 2004/0147928 A1 | 7/2004 | Landry et al. |
| 7,563,274 B2 | 7/2009 | Justis et al. | | 2004/0147929 A1 | 7/2004 | Biedermann et al. |

| | | | | | | |
|---|---|---|---|---|---|---|
| 2004/0158247 A1 | 8/2004 | Sitiso et al. | | 2005/0251139 A1 | 11/2005 | Roh |
| 2004/0162560 A1 | 8/2004 | Raynor et al. | | 2005/0251140 A1 | 11/2005 | Shaolian et al. |
| 2004/0172022 A1 | 9/2004 | Landry et al. | | 2005/0251141 A1 | 11/2005 | Frigg et al. |
| 2004/0172025 A1 | 9/2004 | Drewry et al. | | 2005/0260058 A1 | 11/2005 | Casagne, III |
| 2004/0176766 A1 | 9/2004 | Shluzas | | 2005/0261685 A1 | 11/2005 | Fortin et al. |
| 2004/0186473 A1 | 9/2004 | Cournoyer et al. | | 2005/0261687 A1 | 11/2005 | Garamszegi et al. |
| 2004/0210216 A1 | 10/2004 | Farris et al. | | 2005/0267470 A1 | 12/2005 | McBride |
| 2004/0220567 A1 | 11/2004 | Eisermann et al. | | 2005/0267471 A1 | 12/2005 | Biedermann et al. |
| 2004/0220671 A1 | 11/2004 | Ralph et al. | | 2005/0267474 A1 | 12/2005 | Dalton |
| 2004/0225289 A1 | 11/2004 | Biedermann et al. | | 2005/0267477 A1 | 12/2005 | Jackson |
| 2004/0236327 A1 | 11/2004 | Paul et al. | | 2005/0273099 A1 | 12/2005 | Baccelli et al. |
| 2004/0236328 A1 | 11/2004 | Paul et al. | | 2005/0273101 A1 | 12/2005 | Schumacher |
| 2004/0236329 A1 | 11/2004 | Panjabi | | 2005/0277919 A1 | 12/2005 | Slivka et al. |
| 2004/0236330 A1 | 11/2004 | Purcell et al. | | 2005/0277922 A1 | 12/2005 | Trieu et al. |
| 2004/0249380 A1 | 12/2004 | Glascott | | 2005/0277923 A1 | 12/2005 | Sweeney |
| 2004/0260283 A1 | 12/2004 | Wu et al. | | 2005/0277925 A1 | 12/2005 | Mujwid |
| 2004/0267264 A1 | 12/2004 | Konieczynski et al. | | 2005/0277927 A1 | 12/2005 | Guenther et al. |
| 2005/0027296 A1 | 2/2005 | Thramann et al. | | 2005/0277928 A1 | 12/2005 | Boschert |
| 2005/0033298 A1 | 2/2005 | Hawkes et al. | | 2005/0277931 A1 | 12/2005 | Sweeney et al. |
| 2005/0038432 A1 | 2/2005 | Shaolian et al. | | 2005/0277934 A1 | 12/2005 | Vardiman |
| 2005/0049708 A1 | 3/2005 | Atkinson et al. | | 2005/0283152 A1 | 12/2005 | Lindemann et al. |
| 2005/0055026 A1 | 3/2005 | Biedermann et al. | | 2005/0283157 A1 | 12/2005 | Coates et al. |
| 2005/0065514 A1 | 3/2005 | Studer | | 2005/0283238 A1 | 12/2005 | Reiley |
| 2005/0065515 A1 | 3/2005 | Jahng | | 2005/0283244 A1 | 12/2005 | Gordon et al. |
| 2005/0065516 A1 | 3/2005 | Jahng | | 2005/0288669 A1 | 12/2005 | Abdou |
| 2005/0065517 A1 | 3/2005 | Chin | | 2005/0288670 A1 | 12/2005 | Panjabi |
| 2005/0070899 A1 | 3/2005 | Doubler et al. | | 2005/0288671 A1 | 12/2005 | Yuan et al. |
| 2005/0080415 A1 | 4/2005 | Keyer et al. | | 2005/0288672 A1 | 12/2005 | Ferree |
| 2005/0085812 A1 | 4/2005 | Sherman | | 2005/0288673 A1 | 12/2005 | Catbagan et al. |
| 2005/0085813 A1 | 4/2005 | Spitler et al. | | 2006/0004357 A1 | 1/2006 | Lee et al. |
| 2005/0085815 A1 | 4/2005 | Harms et al. | | 2006/0004359 A1 | 1/2006 | Kramer et al. |
| 2005/0085816 A1 | 4/2005 | Michelson | | 2006/0004360 A1 | 1/2006 | Kramer et al. |
| 2005/0096652 A1 | 5/2005 | Burton | | 2006/0004363 A1 | 1/2006 | Brockmeyer et al. |
| 2005/0096654 A1 | 5/2005 | Lin | | 2006/0009767 A1 | 1/2006 | Kiester |
| 2005/0107788 A1 | 5/2005 | Beaurain et al. | | 2006/0009768 A1 | 1/2006 | Ritland |
| 2005/0113927 A1 | 5/2005 | Malek | | 2006/0009769 A1 | 1/2006 | Liebermann |
| 2005/0124991 A1 | 6/2005 | Jahng | | 2006/0009770 A1 | 1/2006 | Speirs et al. |
| 2005/0131404 A1 | 6/2005 | Mazda et al. | | 2006/0009775 A1 | 1/2006 | Dec et al. |
| 2005/0131407 A1 | 6/2005 | Sicvol et al. | | 2006/0009780 A1 | 1/2006 | Foley et al. |
| 2005/0131413 A1 | 6/2005 | O'Driscoll et al. | | 2006/0009846 A1 | 1/2006 | Trieu et al. |
| 2005/0137597 A1 | 6/2005 | Butler et al. | | 2006/0015099 A1 | 1/2006 | Cannon et al. |
| 2005/0143737 A1 | 6/2005 | Pafford et al. | | 2006/0015104 A1 | 1/2006 | Dalton |
| 2005/0143823 A1 | 6/2005 | Boyd et al. | | 2006/0025767 A1 | 2/2006 | Khalili |
| 2005/0149020 A1 | 7/2005 | Jahng | | 2006/0025768 A1 | 2/2006 | Iott et al. |
| 2005/0149023 A1 | 7/2005 | Ritland | | 2006/0025770 A1 | 2/2006 | Schlapfer et al. |
| 2005/0154389 A1 | 7/2005 | Selover et al. | | 2006/0030850 A1 | 2/2006 | Keegan et al. |
| 2005/0154390 A1 | 7/2005 | Biedermann et al. | | 2006/0036240 A1 | 2/2006 | Colleran et al. |
| 2005/0154391 A1 | 7/2005 | Doherty et al. | | 2006/0036242 A1 | 2/2006 | Nilsson et al. |
| 2005/0159750 A1 | 7/2005 | Doherty | | 2006/0036244 A1 | 2/2006 | Spitler et al. |
| 2005/0165396 A1 | 7/2005 | Fortin et al. | | 2006/0036246 A1 | 2/2006 | Carl et al. |
| 2005/0165400 A1 | 7/2005 | Fernandez | | 2006/0036252 A1 | 2/2006 | Baynham et al. |
| 2005/0171540 A1 | 8/2005 | Lim et al. | | 2006/0036254 A1 | 2/2006 | Lim |
| 2005/0171543 A1 | 8/2005 | Timm et al. | | 2006/0036256 A1 | 2/2006 | Carl et al. |
| 2005/0177157 A1 | 8/2005 | Jahng | | 2006/0036259 A1 | 2/2006 | Carl et al. |
| 2005/0182401 A1 | 8/2005 | Timm et al. | | 2006/0036260 A1 | 2/2006 | Runco et al. |
| 2005/0187548 A1 | 8/2005 | Butler et al. | | 2006/0036323 A1 | 2/2006 | Carl et al. |
| 2005/0187555 A1 | 8/2005 | Biedermann et al. | | 2006/0036324 A1 | 2/2006 | Sachs et al. |
| 2005/0192571 A1 | 9/2005 | Abdelgany | | 2006/0041259 A1 | 2/2006 | Paul et al. |
| 2005/0192580 A1 | 9/2005 | Dalton | | 2006/0052780 A1 | 3/2006 | Errico et al. |
| 2005/0203511 A1 | 9/2005 | Wilson-MacDonald et al. | | 2006/0052783 A1 | 3/2006 | Dant et al. |
| 2005/0203513 A1 | 9/2005 | Jahng et al. | | 2006/0052784 A1 | 3/2006 | Dant et al. |
| 2005/0203514 A1 | 9/2005 | Jahng et al. | | 2006/0052786 A1 | 3/2006 | Dant et al. |
| 2005/0203516 A1 | 9/2005 | Biedermann et al. | | 2006/0058788 A1 | 3/2006 | Hammer et al. |
| 2005/0203517 A1 | 9/2005 | Jahng et al. | | 2006/0058790 A1 | 3/2006 | Carl et al. |
| 2005/0203518 A1 | 9/2005 | Biedermann et al. | | 2006/0064090 A1 | 3/2006 | Park |
| 2005/0203519 A1 | 9/2005 | Harms et al. | | 2006/0064091 A1 | 3/2006 | Ludwig et al. |
| 2005/0216001 A1 | 9/2005 | David | | 2006/0064092 A1 | 3/2006 | Howland |
| 2005/0216003 A1 | 9/2005 | Beiderman et al. | | 2006/0069390 A1 | 3/2006 | Frigg |
| 2005/0228501 A1 | 10/2005 | Miller et al. | | 2006/0074419 A1 | 4/2006 | Taylor et al. |
| 2005/0234450 A1 | 10/2005 | Barker | | 2006/0079894 A1 | 4/2006 | Colleran et al. |
| 2005/0234451 A1 | 10/2005 | Markworth | | 2006/0079895 A1 | 4/2006 | McLeer |
| 2005/0234452 A1 | 10/2005 | Malandain | | 2006/0079896 A1 | 4/2006 | Kwak |
| 2005/0234453 A1 | 10/2005 | Shaolian et al. | | 2006/0079898 A1 | 4/2006 | Ainsworth |
| 2005/0234454 A1 | 10/2005 | Chin | | 2006/0079899 A1 | 4/2006 | Ritland |
| 2005/0234456 A1 | 10/2005 | Malandain | | 2006/0084977 A1 | 4/2006 | Liebermann |
| 2005/0240181 A1 | 10/2005 | Boomer et al. | | 2006/0084981 A1 | 4/2006 | Shluzas |
| 2005/0240183 A1 | 10/2005 | Vaughan | | 2006/0084982 A1 | 4/2006 | Kim |
| 2005/0245930 A1 | 11/2005 | Timm et al. | | 2006/0084983 A1 | 4/2006 | Kim |
| 2005/0251137 A1 | 11/2005 | Ball | | 2006/0084984 A1 | 4/2006 | Kim |

| | | | | | | |
|---|---|---|---|---|---|---|
| 2006/0084985 A1 | 4/2006 | Kim | | 2006/0247632 A1 | 11/2006 | Winslow |
| 2006/0084987 A1 | 4/2006 | Kim | | 2006/0247633 A1 | 11/2006 | Winslow |
| 2006/0084988 A1 | 4/2006 | Kim | | 2006/0247635 A1 | 11/2006 | Gordon |
| 2006/0084989 A1 | 4/2006 | Dickinson et al. | | 2006/0247636 A1 | 11/2006 | Yuan et al. |
| 2006/0084991 A1 | 4/2006 | Borgstrom | | 2006/0247637 A1 | 11/2006 | Colleran |
| 2006/0084993 A1 | 4/2006 | Landry et al. | | 2006/0247779 A1 | 11/2006 | Gordon |
| 2006/0084995 A1 | 4/2006 | Biedermann et al. | | 2006/0264933 A1 | 11/2006 | Baker et al. |
| 2006/0085069 A1 | 4/2006 | Kim | | 2006/0264934 A1 | 11/2006 | Fallin |
| 2006/0089643 A1 | 4/2006 | Mujwid | | 2006/0264935 A1 | 11/2006 | White |
| 2006/0089644 A1 | 4/2006 | Felix | | 2006/0264936 A1 | 11/2006 | Partin et al. |
| 2006/0095037 A1 | 5/2006 | Jones et al. | | 2006/0264937 A1 | 11/2006 | White |
| 2006/0106380 A1 | 5/2006 | Colleran et al. | | 2006/0264940 A1 | 11/2006 | Hartmannt |
| 2006/0106381 A1 | 5/2006 | Ferree | | 2006/0264942 A1 | 11/2006 | Lim et al. |
| 2006/0106383 A1 | 5/2006 | Biedermann et al. | | 2006/0264962 A1 | 11/2006 | Chin et al. |
| 2006/0111714 A1 | 5/2006 | Foley | | 2006/0269940 A1 | 11/2006 | Harman |
| 2006/0111715 A1 | 5/2006 | Jackson | | 2006/0276787 A1 | 12/2006 | Zubok et al. |
| 2006/0116677 A1 | 6/2006 | Burd et al. | | 2006/0276789 A1 | 12/2006 | Jackson |
| 2006/0122597 A1 | 6/2006 | Jojnes et al. | | 2006/0276791 A1 | 12/2006 | Shluzas |
| 2006/0122599 A1 | 6/2006 | Drewry | | 2006/0276792 A1 | 12/2006 | Ensign et al. |
| 2006/0129147 A1 | 6/2006 | Biedermann et al. | | 2006/0282074 A1 | 12/2006 | Renaud et al. |
| 2006/0129149 A1 | 6/2006 | Iott et al. | | 2006/0282075 A1 | 12/2006 | Labrom |
| 2006/0129239 A1 | 6/2006 | Kwak | | 2006/0282076 A1 | 12/2006 | Labrom |
| 2006/0142758 A1 | 6/2006 | Petit | | 2006/0282077 A1 | 12/2006 | Labrom |
| 2006/0142760 A1 | 6/2006 | McDonnell | | 2006/0282078 A1 | 12/2006 | Labrom |
| 2006/0142761 A1 | 6/2006 | Landry et al. | | 2006/0282079 A1 | 12/2006 | Labrom |
| 2006/0149228 A1 | 7/2006 | Schlapfer | | 2006/0282080 A1 | 12/2006 | Albert |
| 2006/0149229 A1 | 7/2006 | Kwak | | 2006/0293657 A1 | 12/2006 | Hartmann |
| 2006/0149232 A1 | 7/2006 | Sasing | | 2006/0293659 A1 | 12/2006 | Alvarez |
| 2006/0149238 A1 | 7/2006 | Sherman et al. | | 2006/0293663 A1 | 12/2006 | Walkenhorst |
| 2006/0149241 A1 | 7/2006 | Richelsoph et al. | | 2006/0293665 A1 | 12/2006 | Shluzas |
| 2006/0149244 A1 | 7/2006 | Amrein et al. | | 2006/0293666 A1 | 12/2006 | Matthis et al. |
| 2006/0155277 A1 | 7/2006 | Metz-Stavenhagen | | 2007/0005062 A1 | 1/2007 | Lange |
| 2006/0155278 A1 | 7/2006 | Warnick | | 2007/0005063 A1 | 1/2007 | Bruneau |
| 2006/0161152 A1 | 7/2006 | Ensign et al. | | 2007/0005137 A1 | 1/2007 | Kwak |
| 2006/0167454 A1 | 7/2006 | Ludwig et al. | | 2007/0016188 A1 | 1/2007 | Boehm, Jr. et al. |
| 2006/0167455 A1 | 7/2006 | Clement et al. | | 2007/0016190 A1 | 1/2007 | Martinez |
| 2006/0173454 A1 | 8/2006 | Spitler et al. | | 2007/0016193 A1 | 1/2007 | Ritland |
| 2006/0173456 A1 | 8/2006 | Hawkes et al. | | 2007/0016194 A1 | 1/2007 | Shaolian et al. |
| 2006/0184171 A1 | 8/2006 | Biedermann | | 2007/0016198 A1 | 1/2007 | Boehm, Jr. et al. |
| 2006/0184180 A1 | 8/2006 | Augostino | | 2007/0016199 A1 | 1/2007 | Boehm, Jr. et al. |
| 2006/0189983 A1 | 8/2006 | Falin | | 2007/0021750 A1 | 1/2007 | Shluzas et al. |
| 2006/0189984 A1 | 8/2006 | Fallin | | 2007/0043355 A1 | 2/2007 | Bette et al. |
| 2006/0189985 A1 | 8/2006 | Lewis | | 2007/0043356 A1 | 2/2007 | Timm |
| 2006/0195090 A1 | 8/2006 | Suddaby | | 2007/0043357 A1 | 2/2007 | Kirschman |
| 2006/0195093 A1 | 8/2006 | Jahng | | 2007/0043358 A1 | 2/2007 | Molz, IV et al. |
| 2006/0195098 A1 | 8/2006 | Schumacher | | 2007/0043359 A1 | 2/2007 | Altarac et al. |
| 2006/0200128 A1 | 9/2006 | Mueller | | 2007/0043364 A1 | 2/2007 | Cawley et al. |
| 2006/0200130 A1 | 9/2006 | Hawkins | | 2007/0049931 A1 | 3/2007 | Justis et al. |
| 2006/0200131 A1 | 9/2006 | Chao et al. | | 2007/0049933 A1 | 3/2007 | Ahn et al. |
| 2006/0200132 A1 | 9/2006 | Chao et al. | | 2007/0049936 A1 | 3/2007 | Colleran |
| 2006/0200135 A1 | 9/2006 | Sherman et al. | | 2007/0055235 A1 | 3/2007 | Janowski et al. |
| 2006/0200138 A1 | 9/2006 | Michelson | | 2007/0055236 A1 | 3/2007 | Hudgins |
| 2006/0200139 A1 | 9/2006 | Michelson | | 2007/0055238 A1 | 3/2007 | Biedermann et al. |
| 2006/0200149 A1 | 9/2006 | Hoy et al. | | 2007/0055239 A1 | 3/2007 | Sweeney et al. |
| 2006/0210494 A1 | 9/2006 | Rabiei et al. | | 2007/0055240 A1 | 3/2007 | Matthis et al. |
| 2006/0212033 A1 | 9/2006 | Rothman | | 2007/0055241 A1 | 3/2007 | Matthis et al. |
| 2006/0212034 A1 | 9/2006 | Triplett et al. | | 2007/0055242 A1 | 3/2007 | Bailly |
| 2006/0217713 A1 | 9/2006 | Serhan et al. | | 2007/0055244 A1 | 3/2007 | Jackson |
| 2006/0217714 A1 | 9/2006 | Serhan et al. | | 2007/0055247 A1 | 3/2007 | Jahng |
| 2006/0217716 A1 | 9/2006 | Baker et al. | | 2007/0073289 A1 | 3/2007 | Kwak |
| 2006/0217719 A1 | 9/2006 | Albert et al. | | 2007/0073290 A1 | 3/2007 | Boehm, Jr. |
| 2006/0229608 A1 | 10/2006 | Foster | | 2007/0073291 A1 | 3/2007 | Cordaro et al. |
| 2006/0229609 A1 | 10/2006 | Wang | | 2007/0073293 A1 | 3/2007 | Martz |
| 2006/0229612 A1 | 10/2006 | Rothman | | 2007/0073294 A1 | 3/2007 | Chin et al. |
| 2006/0229613 A1 | 10/2006 | Timm | | 2007/0078460 A1 | 4/2007 | Frigg et al. |
| 2006/0229614 A1 | 10/2006 | Foley et al. | | 2007/0078461 A1 | 4/2007 | Shluzas |
| 2006/0229615 A1 | 10/2006 | Abdou | | 2007/0083199 A1 | 4/2007 | Baccelli |
| 2006/0235389 A1 | 10/2006 | Albert et al. | | 2007/0088357 A1 | 4/2007 | Johnson et al. |
| 2006/0235392 A1 | 10/2006 | Hammer et al. | | 2007/0088359 A1 | 4/2007 | Woods et al. |
| 2006/0235393 A1 | 10/2006 | Bono et al. | | 2007/0093813 A1 | 4/2007 | Callahan, II et al. |
| 2006/0241593 A1 | 10/2006 | Sherman et al. | | 2007/0093814 A1 | 4/2007 | Callahan, II et al. |
| 2006/0241595 A1 | 10/2006 | Molz, IV et al. | | 2007/0093815 A1 | 4/2007 | Callahan, II et al. |
| 2006/0241599 A1 | 10/2006 | Konieczynski et al. | | 2007/0093817 A1 | 4/2007 | Barrus et al. |
| 2006/0241600 A1 | 10/2006 | Ensign et al. | | 2007/0093818 A1 | 4/2007 | Biedermann et al. |
| 2006/0241769 A1 | 10/2006 | Gordon | | 2007/0093819 A1 | 4/2007 | Albert |
| 2006/0241771 A1 | 10/2006 | Gordon | | 2007/0093824 A1 | 4/2007 | Hestad et al. |
| 2006/0247624 A1 | 11/2006 | Banouskou et al. | | 2007/0093826 A1 | 4/2007 | Hawkes et al. |
| 2006/0247630 A1 | 11/2006 | Iott et al. | | 2007/0093827 A1 | 4/2007 | Warnick |
| 2006/0247631 A1 | 11/2006 | Ahn et al. | | 2007/0093828 A1 | 4/2007 | Abdou |

| | | |
|---|---|---|
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0124249 A1 | 11/2007 | Lim et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154307 A1 | 6/2008 | Colleran et al. |
| 2008/0161854 A1 | 7/2008 | Bae et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Bosehert |
| 2008/0234739 A1 | 9/2008 | Hudgins et al. |

| | | |
|---|---|---|
| 2008/0234744 A1 | 9/2008 | Zylber et al. |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2009/0005817 A1 | 1/2009 | Friedrich et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durwood et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0082071 A1 | 4/2010 | Moumene et al. |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0094348 A1 | 4/2010 | Biedermann et al. |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 1519139 | 7/1978 |
| GB | 9202745.8 | 4/1992 |
| GB | 2365345 | 2/2002 |
| GB | 2382304 | 5/2003 |
| JP | 10277070 | 10/1998 |
| JP | 2000325358 | 3/2000 |
| JP | SP2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO96/41582 | 12/1996 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |

| | | |
|---|---|---|
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/013839 | 2/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | 2006/028537 | 3/2006 |
| WO | WO2006/028537 | 3/2006 |
| WO | WO2006/045094 | 4/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

*Claris Instrumentation* Brochure, G Med, pub. 1997.
*VLS System Variable Locking Screw* Brochure, Interpore Cross International, 1999.
*The Rod Plate System* Brochure, Stryker Howmedica Osteonics, pub. Oct. 1999.
*SDRS Surgical Dynamics Rod System* Brochure, Surgical Dynamics, pub. 1998-99.
*Versalok Low Back Fixation System* Brochure, Wright Medical Technology, Inc., pub. 1997.
Brochure of Tyco/Healthcare/Surgical Dynamics on Spiral Radius 90D, Publication Date: Sep. 2001, pp. 1-8.
Brochure of Sofamor Danek the Spine Specialist, TSRH, Pedicle Screw Spinal System, Publication Date: Jan. 23, 1995.
Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
Brochure of Zimmer Spine, Inc., Dynesys® LIS Less Invasive Surgery, The Dynamic Stabilization System, Publication Date: 2005.

* cited by examiner

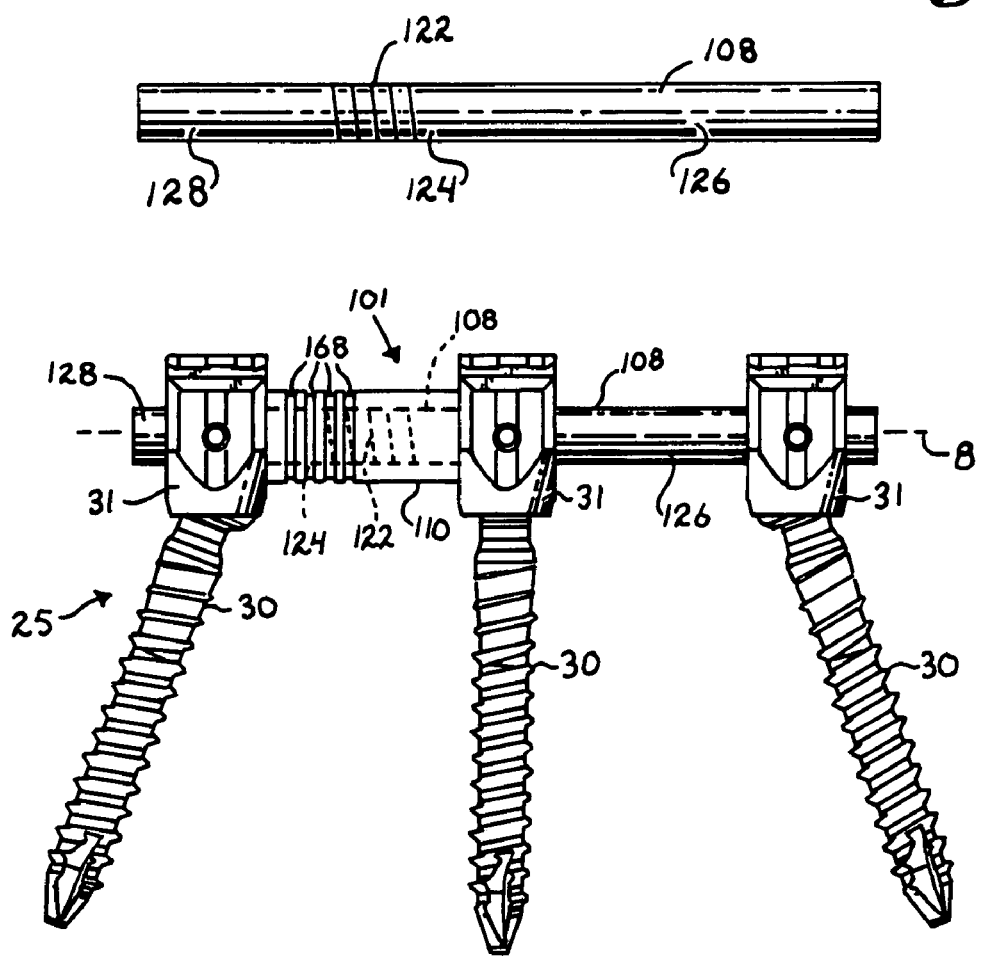

DYNAMIC STABILIZATION CONNECTING MEMBER WITH SLITTED CORE AND OUTER SLEEVE

CROSS REFERENCE TO RELATED APPLICATIONS

This application claims the benefit of U.S. Provisional Application No. 60/850,464 filed Oct. 10, 2006, the disclosure of which is incorporated by reference herein. This application is also a continuation-in-part of U.S. patent application Ser. No. 11/522,503, filed Sep. 14, 2006 that claims the benefit of U.S. Provisional Application Nos. 60/722,300, filed Sep. 30, 2005; 60/725,445, filed Oct. 11, 2005; 60/728,912, filed Oct. 21, 2005; 60/736,112, filed Nov. 10, 2005, and 60/832,644, filed Jul. 21, 2006; the disclosures all of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter, width or cross-sectional area of a size to provide substantially rigid support in all planes with varying degrees of rigidity.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including soft tissue ingrowth with scarring, lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a synthetic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the chord or strand in the bone anchors. Although flexible, the cords or strands utilized in such systems do not allow for elastic distraction or stretchability of the system once implanted because the cord or strand must be stretched or pulled to maximum tension in order to provide a stable, supportive system.

The complex dynamic conditions associated with spinal movement therefore provide quite a challenge for the design of elongate elastic longitudinal connecting members that exhibit an adequate fatigue strength to provide stabilization and protected motion of the spine, without fusion, and allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protected segmental spinal movement.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A longitudinal connecting member assembly according to the invention has an inner integral core or bar, a portion thereof having a slit. The slit is preferably helical. An outer sleeve or spacer surrounds the slitted portion of the core and is located entirely outside of a periphery of the slitted core or bar. In a preferred embodiment, the sleeve extends between a pair of adjacent bone anchors and has a cylindrical cross-sectional shape. The slitted core and outer sleeve cooperate dynamically, both features having some flexibility, with the outer sleeve primarily protecting and limiting flexing movement of the inner core. The outer sleeve may include a grooved portion that may be compressed upon installation between two bone anchors. As compared to dynamic systems that include flexible cords and spacers, embodiments according to the present invention advantageously allow for elastic distraction, elongation or stretchability of the connecting member assembly.

A variety of embodiments according to the invention are possible. For example, the inner core may extend between three or more bone anchors with some or all of the sections that are located between bone anchors having a slit and cooperating sleeve. Alternatively some of the sections may be of a more rigid construction and not include slits and sleeves.

OBJECTS AND ADVANTAGES OF THE INVENTION

Therefore, it is an object of the present invention to overcome one or more of the problems with bone attachment assemblies described above. An object of the invention is to provide dynamic medical implant stabilization assemblies having longitudinal connecting members that include an integral inner core having a flexible portion that allows for bending, torsion, compression and distraction of the assembly. Another object of the invention is to provide such an assembly wherein the flexible portion is insertable into a protective outer sleeve. A further object of the invention is to provide such an assembly wherein the outer sleeve is compressed upon installation, without having to directly tension the inner core, by compressing the bone anchors toward one another. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion being integral with and adjacent to the core having the flexible portion. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 10 is a front elevational view of a second embodiment of an inner core according to the invention having a slitted portion and a solid portion.

FIG. 11 is a front elevational view of a second longitudinal connecting member assembly according to the invention having the inner core of FIG. 10, an outer sleeve cooperating with the slitted portion and three bone screws.

DETAILED DESCRIPTION OF THE INVENTION

Figure 1:
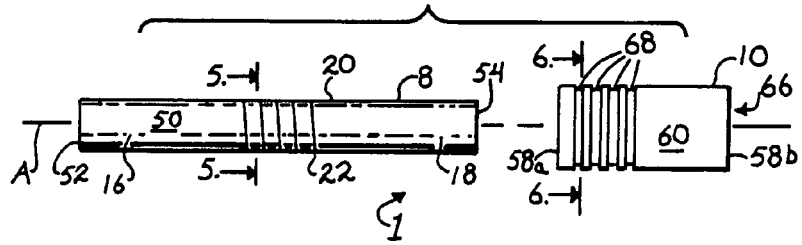
FIG. 1 is an exploded front elevational view of a dynamic fixation connecting member assembly according to the invention including an inner core with a helical slit and an outer sleeve.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-9, the reference numeral 1 generally designates a non-fusion dynamic stabilization longitudinal connecting member assembly according to the present invention. The connecting member assembly 1 includes an inner core 8 and an outer sleeve or spacer 10. The inner core 8 is elongate, either linear or curvilinear, having a central longitudinal axis A and also including a first end portion or section 16 extending along the axis A, an opposite second end portion or section 18 and a mid-portion or section 20 having a helical slit 22. The inner core 8 is receivable in the flexible outer sleeve 10, with the sleeve 10 ultimately surrounding the slitted mid-portion 20 as will be described more fully below. The dynamic connecting member assembly 1 cooperates with at least a pair of bone anchors, such as the polyaxial bone screws, generally 25 and cooperating closure structures 27 shown in the drawings, the assembly 1 being captured and fixed in place at the end portions 16 and 18 by cooperation between the bone screws 25 and the closure structures 27. The sleeve 10 is sized and shaped to fit between pairs of bone screws 25 or other bone anchors, cooperating with the inner core 8 to support adjacent vertebrae. The sleeve 10 can be of any cross-sectional shape and can be cut to fit any needed length.

Because the end portions 16 and 18 are substantially solid and, in this illustrated embodiment, cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, instabilities, injuries, or defects (congenital, developmental) to the spinal column of a patient. The end portions 16 and 18 can be of any length and the helical slit section can also vary in length.

The illustrated polyaxial bone screw 25 includes a shank 30 for insertion into a vertebra (not shown), the shank 30 being pivotally attached to an open receiver or head 31. The shank 30 includes a threaded outer surface and a central cannula or through-bore 32 disposed along an axis of rotation of the shank, the through-bore 32 extending between a top surface 33 and a bottom surface 34 of the shank 30. The bore 32 provides a passage through the shank interior for a length of wire or pin inserted into the vertebra prior to the insertion of the shank 30, the wire or pin providing a guide for insertion of the shank 30 into the vertebra.

The receiver 31 has a pair of spaced and generally parallel arms 35 that form an open generally U-shaped channel 37 therebetween that is open at distal ends of the arms 35. The arms 35 each include radially inward or interior surfaces 40 that have a discontinuous guide and advancement structure mateable with cooperating structure on the closure structure 27. In the illustrated embodiment, the guide and advancement structure is a partial helically wound flangeform configured to mate under rotation with a similar structure on the closure structure 27. However, it is foreseen that the guide and advancement structure could alternatively be a buttress thread, a square thread, a reverse angle thread or other thread like or non-thread like helically wound advancement structures for operably guiding under rotation and advancing the closure structure 27 downward between the receiver arms 35 and having such a nature as to resist splaying of the arms 35 when the closure 27 is advanced into the U-shaped channel 37.

Each of the arms 35 also includes a V-shaped or undercut tool engagement groove 41 formed on a substantially planar outer surface thereof which may be used for holding the receiver 31 with a holding tool (not shown) having projections that are received within the grooves 41 during implantation of the shank 30 into the vertebra (not shown). The grooves 41 may also cooperate with a holding tool during bone screw assembly and during subsequent installation of the connecting member assembly 1 and the closure structure 27. It is foreseen that tool receiving grooves or apertures may be configured in a variety of shapes and sizes and be disposed at other locations on the receiver arms 35.

The shank 30 and the receiver 31 may be attached in a variety of ways. For example, a spline capture connection as described in U.S. Pat. No. 6,716,214, and incorporated by reference herein, is shown in the drawing figures wherein the bone screw shank 30 includes a capture structure 42 mateable with a retaining structure 44 disposed within the receiver. The retaining structure 44 includes a partially spherical surface that is slidingly mateable with a cooperating inner surface of the receiver 31, allowing for a wide range of pivotal movement between the shank 30 and the receiver 31. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member or may include compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. Furthermore, although the closure structure 27 of the present invention is illustrated with the polyaxial bone screw 25 having an open receiver or head 31, it foreseen that a variety of closure structure may be used in conjunction with any type of medical implant having an open or closed head, including monoaxial bone screws, hinged bone screws, hooks and the like used in spinal surgery.

To provide a biologically active interface with the bone, the threaded shank 30 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The longitudinal connecting member assembly 1 illustrated in FIGS. 1-9 is elongate, with the inner core 8 being made from metal, metal alloys or other suitable materials, including plastic polymers such as polyetheretherketone (PEEK), ultra-high-molecular weight-polyethylene (UHMWP), polyurethanes and composites. The outer sleeve or spacer 10 may be made of a variety of materials including metals, plastics and composites. The illustrated sleeve 10 is made from a plastic, such as a thermoplastic elastomer, for example, polycarbonate-urethane. In order to reduce the production of micro wear debris, that in turn may cause inflammation, it is desirable to make the inner core 8 from a different material than the sleeve 10. Additionally or alternatively, in order to result in adequate hardness and low or no wear debris, the sleeve 10 inner surfaces and cooperating core 8 outer surfaces may be coated with an ultra thin, ultra hard, ultra slick and ultra smooth coating, such as may be obtained from ion bonding techniques and/or other gas or chemical treatments.

Specifically, with the exception of the slitted mid portion 20, the illustrated core 8 is a substantially solid, smooth and uniform cylinder or rod having an outer cylindrical surface 50 and a circular cross-section. It is foreseen that in some embodiments, the core 8 may be substantially hollow, having a bore extending along the axis A all or part of an entire length of the core 8. The illustrated core 8 has an end 52 and an opposite end 54, with the solid end portion 16 terminating at the end 52 and the solid end portion 18 terminating at the end 54. The portions 16 and 18 are each sized and shaped to be received in the U-shaped channel 37 of a bone screw assembly 25 with the mid-portion 20 sized and shaped to extend between cooperating bone screws 25. It is foreseen that the core could be non-cylindrical in shape and in cross-section and that it can be cut to length to fit any clinical application.

Figure 3:
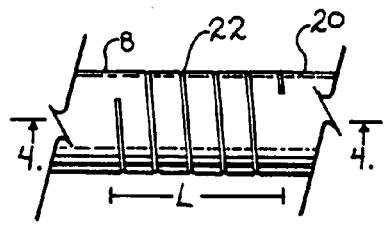
FIG. 3 is an enlarged and partial front elevational view of a portion of the inner core of FIG. 1.
Figure 4:
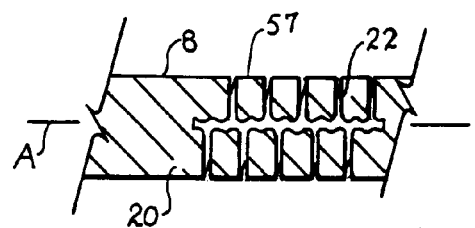
FIG. 4 is an enlarged and partial cross-sectional view taken along the line 4-4 of FIG. 3.
Figure 5:
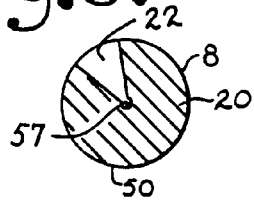
FIG. 5 is an enlarged cross-sectional view of the inner core taken along the line 5-5 of FIG. 1.

With particular reference to FIGS. 3-5, the mid-portion 20 includes the helical slit 22 that is formed in and extends from the outer surface or periphery 50 toward the axis A. In the illustrated embodiment, a process of forming the helical slit 22 creates an aperture, inner space or bore 57 that extends along the axis A along a length L of the slit 22. In embodiments wherein the core 8 already has a through bore extending along the axis A, the helical slit extends through the outer surface 50 and an inner surface that defines such bore. The slit 22 disposed in part or all of the mid-portion 20, results in the mid-portion being coil- or spring-like in nature. Thus, when the core 8 is fixed to bone screws 25 at the end portions 16 and 18 thereof, the slitted mid-portion 20 provides relief (e.g., shock absorption) and limited movement with respect to flexion, extension, torsion, distraction and compressive forces placed on the assembly 1.

The sleeve 10 advantageously cooperates with the core helical slit 22 and is slidable thereon, providing limitation and protection of movement of the core 8 at the slit 22. The sleeve 10 also protects patient body tissue from damage that might otherwise occur in the vicinity of the helical slit 22. The sleeve 10 prevents soft tissue ingrowth into the slit 22 that could hinder the function of the slit 22. The sleeve 10 is sized and shaped for substantially even and precise alignment and substantial compressive contact between flat end surfaces 58a and 58b of the sleeve 10 and cooperating flat side surfaces 59 of the receivers 31. Furthermore, as will be discussed in greater detail below, when the sleeve is implanted, and the closure structures 27 are tightened, the tools utilized to implant the assembly 1 and/or the bone screws 27 are manipulated so as to axially compress the sleeve 10, now substantially coaxial with the core 8 axis A, between facing side surfaces 59 of adjacent receivers 31. Such pre-compression after installation results in some tension and distraction of the slitted mid-portion 20 of the core 8 when the implantation tools are removed from the bone screws 25, as the sleeve surfaces 58a and 58b then press against the facing bone screw surfaces 59, but the core 8 is otherwise fixed with respect to each of the bone screws 27 within the receiver channels 37. Such dynamic tension/compression relationship between the sleeve 10 and the slitted core 8 provides further strength and stability to the overall assembly and also allows for the entire connecting member assembly 1 to elongate, if needed, in response to spinal movement. The increased stability and strength of the assembly advantageously allows for use of a smaller, more compact, reduced volume, lower profile longitudinal connecting member assembly 1 and cooperating bone anchors than, for example, flexible cord and spacer type longitudinal connecting member assemblies. Also this type of assembly using a flexible non-cord like member allows the use of any type of bone anchor, polyaxial or not.

Figure 6:
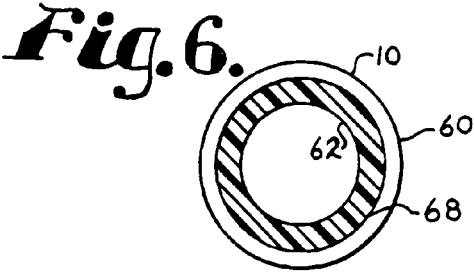
FIG. 6 is an enlarged cross-sectional view of the outer sleeve taken along the line 6-6 of FIG. 1.

In the embodiment shown, the sleeve 10 is also substantially cylindrical with an external substantially cylindrical surface 60 and an internal substantially cylindrical and smooth surface 62. The surface 62 defines a bore 66 with a circular cross section, the bore 66 extending through the sleeve 10. In the illustrated embodiment, the sleeve 10 further includes a plurality of compression grooves 68. Sleeves according to the invention may include one, none or any desired number of grooves 68. Each of the illustrated grooves 68 is substantially uniform and circular in cross-section as illustrated in FIG. 6, being formed in the external surface 60 and extending radially toward the internal surface 62. The internal surface 62 is of a slightly greater diameter than an outer diameter of the cylindrical surface 50 of the core 8, allowing for axially directed sliding movement of the sleeve 10 with respect to the core 8. When the cylindrical core 8 is inserted in the sleeve 10, the sleeve 10 completely surrounds the helical slit 22. It is noted that in addition to limiting the bendability of the core 8 and thus providing strength and stability to the assembly 1, the sleeve 10 also keeps scar tissue from growing into the core 8 through the helical slit 22, thus eliminating the need for a sheath-like structure to be placed, adhered or otherwise applied to the core 8.

The core 8 may be sized and made from such materials as to provide for a relatively more rigid assembly 1 or a relatively more flexible assembly 1 with respect to flex or bendability along the assembly 1. Such flexibility therefore may be varied by changing the outer diameter of the core 8 and thus likewise changing the inner diametric size of the sleeve 10. Also, since the distance between the bone screw assembly receivers or heads can vary, the core 8 may need to be more or less stiff. The pitch of the helical slit 22 may also be varied to provide a more or less flexible core and the shock absorption desired. For example, it is noted that increasing the pitch (i.e., forming a more acute angle between the slant of the slit 22 with respect to the axis A results in a stiffer assembly with respect to bending and axial displacements. Furthermore, a benefit of increasing pitch is a lessening of impact loading between the surfaces defining the helical slit 22, thus dampening the jolts of an impact and improving shock absorption. Again the length of the slitted section can vary.

Figure 7:
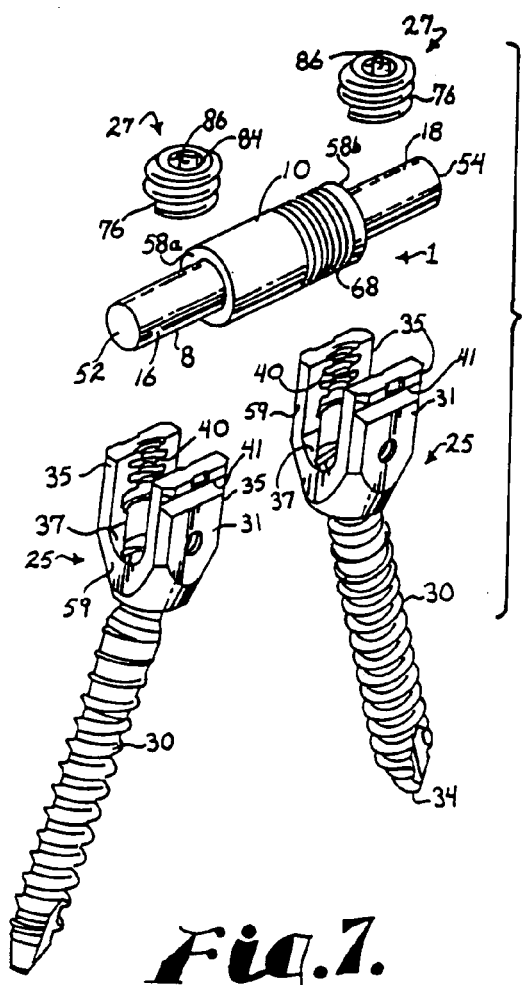
FIG. 7 is an exploded perspective view of the assembly of FIG. 2 showing the dynamic fixation connecting member, the two bone screws and a pair of closure structures.
Figure 8:
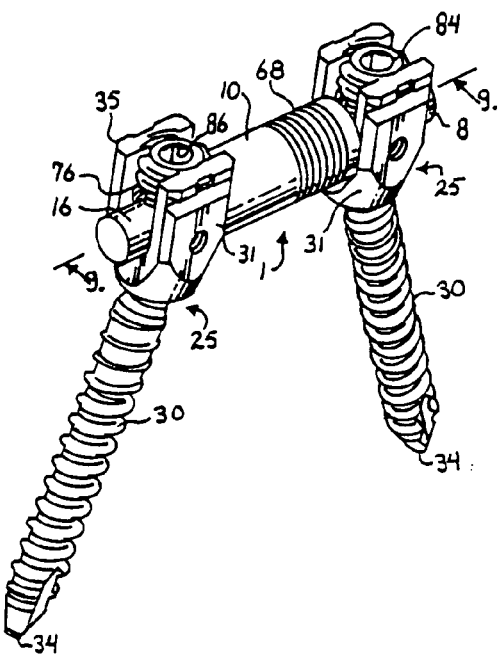
FIG. 8 is a perspective view of the assembly of FIG. 7 shown fully assembled.
Figure 9:
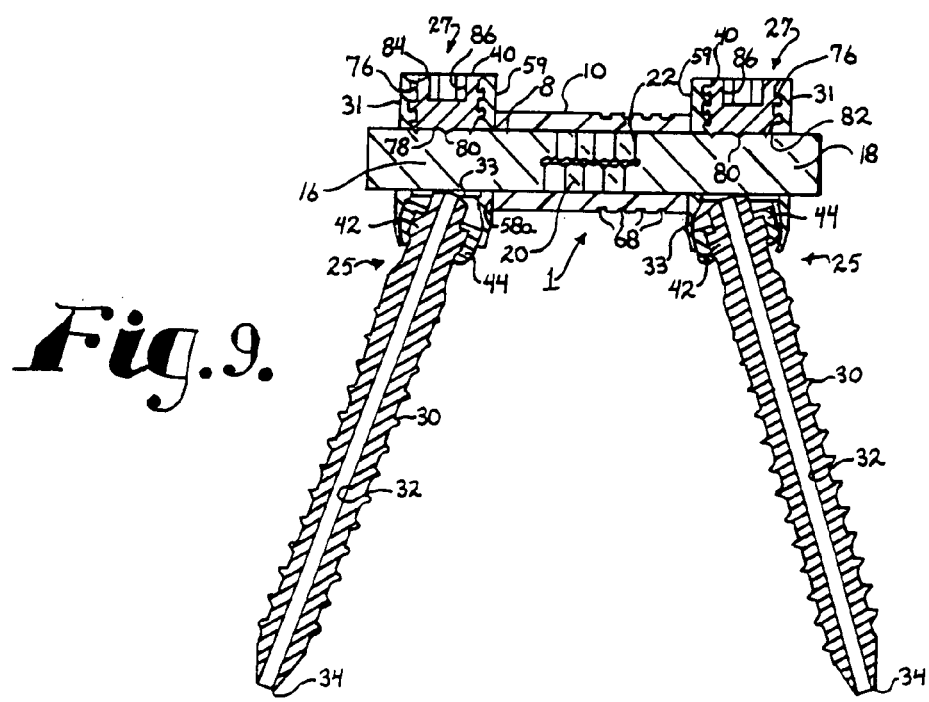
FIG. 9 is an enlarged cross-sectional view taken along the line 9-9 of FIG. 8.

With reference to FIGS. 7-9, the closure structure 27 can be any of a variety of different types of closure structures for use in conjunction with the present invention with suitable mating structure on the interior surface 40 of the upstanding arms 35 of the receiver 31. The illustrated closure structure 27 is rotatable between the spaced arms 35, but could be, for example, a slide-in closure structure or a ninety degree twist-in closure with opposed flange-like or wedge-like projections. The illustrated closure structure 27 is substantially cylindrical and includes an outer helically wound guide and advancement structure in the form of a flange form 76 that operably joins with the guide and advancement structure disposed on the interior 40 of the arms 35. The flange form 76 utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 27 downward between the arms 35 and having such a nature as to resist splaying of the arms 35 when the closure structure 27 is advanced into the U-shaped channel 37.

The illustrated closure structure 27 includes a lower surface 78 that is substantially planar and includes a point 80 and a rim 82 protruding therefrom for engaging the core 8 outer cylindrical surface at the non-slitted end portion 16 or 18. The closure structure 27 has a top surface 84 with an internal drive in the form of an aperture 86, illustrated as a star-shaped internal drive, for example, sold under the trademark TORX. A driving tool (not shown) sized and shaped for engagement with the internal drive 86 is used for both rotatable engagement and, if needed, disengagement of the closure 27 from the arms 35. Although a star-shaped internal drive 86 is shown in the drawings, the tool engagement structure may take a variety of forms and may include, but is not limited to, a hex shape or other features or apertures, such as slotted, tri-wing, spanner, two or more apertures of various shapes, and the like. It is also foreseen that the closure structure 27 may alternatively include a break-off head designed to allow such a head to break from a base of the closure at a preselected torque, for example, 70 to 140 inch pounds. Such a closure structure would also include a base having an internal drive to be used for closure removal.

In use, at least two bone anchor assemblies 25 are implanted into vertebrae for use with the longitudinal connecting member assembly 1. Each vertebra may be pre-drilled to minimize stressing the bone when screws are used. Furthermore, if and when a cannulated bone screw shank is utilized, each vertebra could have a guide wire or pin (not shown) inserted therein that is shaped for the bone screw cannula 32 of the bone screw shank 30 and provides a guide for the placement and angle of the shank 30 with respect to the cooperating vertebra. A further tap hole may be made and the shank 30 is then driven into the vertebra by rotation of a driving tool (not shown) that engages a driving feature near the top 33 of the shank 30 illustrated as a hex-shaped head. It is foreseen that the screws 25 and the longitudinal connecting member 1 can be inserted in a percutaneous or minimally invasive surgical manner.

Figure 2:
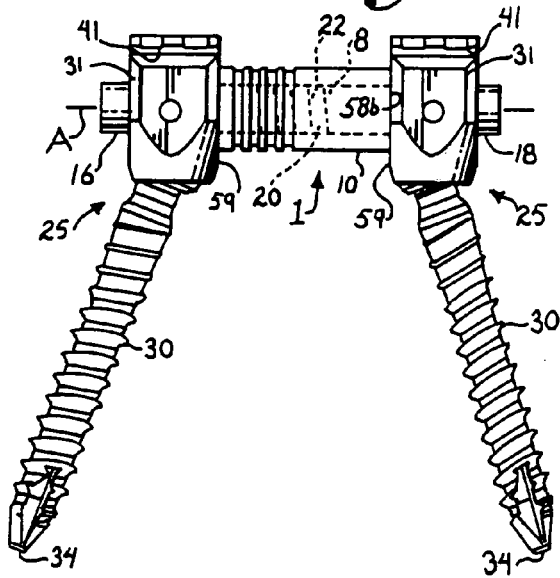
FIG. 2 is a front elevational view of a dynamic fixation assembly according to the invention including the connecting member assembly of FIG. 1 and two bone screws.

With particular reference to FIG. 1, the longitudinal connecting member assembly 1 is assembled by inserting the core 8 into the bore 66 defined by the inner cylindrical surface 62 of the outer sleeve 10 after both the core 8 and the sleeve 10 have been cut to length. The end 54 of the core 8 is placed into the bore 66 at the surface 58a and the sleeve 10 is moved toward the end portion 16 until the sleeve 10 is positioned between the end portions 16 and 18 and is disposed about the mid-portion 20, thus covering or encompassing the helical slit 22. It is noted that the core 8 and the sleeve 10 may also be assembled in other ways, for example, by inserting the end 52 of the core 8 into the sleeve 10 at the end surface 58b. Furthermore, alignment of the slit 22 with respect to the grooves 68 along the axis A as shown, for example, in FIG. 2 is approximate and not intended to limit the relative position or location of the slit 22 with respect to the grooves 68 or the slit with respect to the pair of receivers 31. Such positioning may be determined, for example, in relation to a degree of overall flexibility desired for the assembly 1.

The connecting member assembly 1 is eventually positioned in an open or percutaneous manner in cooperation with the at least two bone anchors or screws 25 with the sleeve 10 disposed between the two bone screws 25 and the end portions 16 and 18 each within the U-shaped channels 37 of the two bone screws 25. Again, the end portions 16 and 18 could extend to other bone anchors. A closure structure 27 is then inserted into and advanced between the arms 35 of each of the bone anchor screws 25. The closure structure 27 is rotated, using a tool engaged with the inner drive 86 until a selected pressure is reached at which point the core 8 is urged toward, but not completely seated in the channel 37. For example, about 80 to about 120 inch pounds pressure may be required for fixing the bone screw shank 30 with respect to the receiver 31.

Downward movement of the closure structure 27 into the channel 37 presses a respective end portion 16 or 18 downward into engagement with a top 33 or other upper portion of the respective bone screw shank 30, pressing the respective retaining structure 44 into engagement with the respective receiver 31, thus setting an angle of articulation of the respective shank 30 with respect to the respective receiver 31, clamping the shank 30 into a fixed position with respect to the receiver 31. The receiver 31, the shank 30 and the retaining structure 44 cooperate in such a manner that the receiver 31 and the shank 30 can be secured at any of a plurality of angles, articulations or rotational alignments relative to one another and within a selected range of angles both from side to side and from front to rear, to enable flexible or articulated engagement of the receiver 31 with the shank 30 until both are locked or fixed relative to each other. Again it is also possible to use fixed or monoaxial screws with the invention, as described below.

Alternatively, it is foreseen that the capture of the connecting member assembly 1 by bone screws or other bone anchors and cooperating closure structures could further involve the use of an upper and/or a lower compression member or insert. Furthermore, the assembly 1 may cooperate with an open receiver that is integral or fixed in position with respect to a bone screw shank or bone hook, or with a receiver having limited angular movement with respect to the shank, such as a hinged connection, also with or without other compression members or inserts for fixing the assembly 1, the receiver and/or the bone anchor in a desired position or orientation with respect to the cooperating vertebrae.

As indicated previously herein, as the closure structures 27 are rotated and then tightened against the end portions 16 and 18 within a pair of spaced bone screws 25, such bone screws 25 may be pressed toward one another, thereby compressing and pre-loading the sleeve 10. When the insertion and tightening tools are removed, the resilient sleeve 10, pressing against facing surfaces 59 of the cooperating bone screw receivers 31, stretches and tensions the mid-portion 20 of the core 8 at the helical slit 22. The assembly 1 is thus substantially dynamically loaded and oriented relative to the cooperating vertebra, providing relief (e.g., shock absorption) and protected movement with respect to flexion, extension, torsional and distraction and compressive forces placed on the assembly 1 and the two connected bone screws 25. Again, the helical slit 22 allows the core 8 to twist or turn, providing relief for torsional stresses. The sleeve 10 can also limit such torsional movement as well as bending movement of the core 8, providing spinal support. Furthermore, because the sleeve 10 is compressed during installation, the sleeve advantageously allows for some protected extension or distraction of both the core 8 and the sleeve 10 as well as compression of the assembly 1 in cooperation with the core 8.

If removal of the assembly 1 from any of the bone screw assemblies 25 is necessary, or if it is desired to release the assembly 1 at a particular location, disassembly is accomplished by using the driving tool (not shown) with a star-shaped driving formation on the closure structure 27 internal drive 86 to rotate and remove the closure structure 27 from the receiver 31. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the inner core 8 end portions 16 and 18, utilizing the same receivers 31 and closure structures 27. Alternatively, if less support is eventually required, a less rigid, more flexible assembly, for example, an assembly 1 made of a more flexible material or an assembly 1 having a slit of different length and/or pitch, but with end portions having the same diameter as the inner core 8 end portions 16 and 18, may replace the assembly 1, also utilizing the same bone screws 25.

With reference to FIGS. 10 and 11, an alternative longitudinal connecting member assembly according to the invention, generally 101 includes an inner core 108 and an outer sleeve 110. The outer sleeve 110 is the same or substantially similar to the sleeve 10 previously described herein. The assembly 101 is shown attached to three bone screw assemblies 25, previously described herein, each bone screw assembly having a shank 30 and a receiver 31, also previously described herein. Although not shown, each bone screw assembly 25 further includes a closure structure 27, also previously described herein. As with the assembly 1, the assembly 101 readily cooperates with a wide variety of bone anchors and closures, also as previously described herein.

The connecting member assembly 101 is sized and shaped to attach to at least three bone screw assemblies 25, to provide a flexible dynamic stabilization length or segment 124 where the core 108 has a slit 122 and cooperates with the sleeve 110. The core length or segment 124 and the slit 122 are similar or nearly identical to the core 8 and sleeve 10, respectively, previously described herein. However, the segment 124 is integral or otherwise fixed to a more rigid length or segment 126 that is of solid construction and may be used in conjunction with spinal fusion along such length. The flexible length 124 that includes the slit 122 is disposed between the rigid length 126 and another shorter rigid length or portion 128 sized and shaped to be received by the third bone screw assembly 25. The sleeve 110 includes grooves 168 the same or substantially similar to the grooves 68 previously described herein with respect to the sleeve 10. Also, in the illustrated embodiment the portion 128 is substantially similar or identical to the end portion 16 previously described herein with respect to the core 8. It is noted that the portion 128 may also be elongate of any length, similar to the length 126, for cooperating with more than one bone anchor or bone screw assembly 25. Thus, an assembly 101 according to the invention may be used to provide protected movement of the spine along the segment 124, spinal fusion along the length 126 and spinal fusion on a length opposite the length 128, if the portion 128 is of sufficient length to attach to another bone screw assembly 25. It is noted that a portion or portions of the assembly 101 can be straight or curved, pre-bent or curvilinear.

In the illustrated embodiment, the portions or segments 124, 126 and 128 are integral and substantially uniform along a central longitudinal axis B thereof, and are cylindrical. The segments 124, 126 and 128 are also of solid construction with the exception of the portion of the segment 124 that has the helical slit 122. As indicated above, the helical slit 122 is similar or identical to the helical slit 22 previously described herein, having features and cross-sections as shown in FIGS. 3, 4 and 5.

In use, the assembly 101 is implanted in a manner substantially similar to that previously described herein with respect to the assembly 1. The segment 126 is ultimately located near a portion of the spine requiring more rigid support while the segment 124 and cooperating sleeve 110 are located near a portion of the spine requiring less support. If desired, during tightening of the closure structures 27 against the core 108, the sleeve 110 is compressed between facing bone screw receivers 31 as previously described herein with respect to the sleeve 10.

It is noted that an advantageous connecting member 101 according to the invention includes a rigid length or segment 126 made from a metal alloy that is elongate and intended for fusion along a major portion or section of the spine, for example, the rigid length 126 may be sized to extend from the sacrum to the thoracic spinal segment T10. Such an elongate portion or segment 126 is thus connectable to a plurality of bone anchors along the spine. Such a connecting member further includes a dynamic section 124 having a slit 122 and spacer or sleeve 110 that is sized for placement, for example, between T9 and T8. Such an embodiment is believed to minimize rapid degeneration and compressive fractures that tend to occur near ends of such elongate connecting member assemblies.

Figure 12:
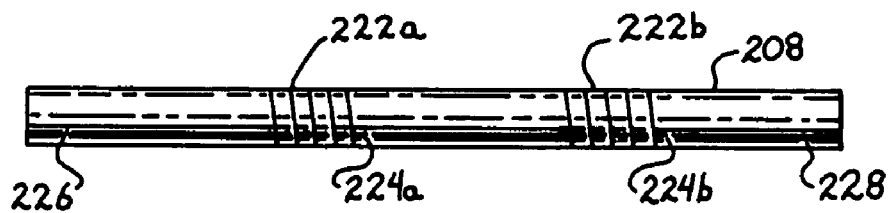
FIG. 12 is a front elevational view of a third embodiment of an inner core according to the invention having a pair of slitted portions.
Figure 13:
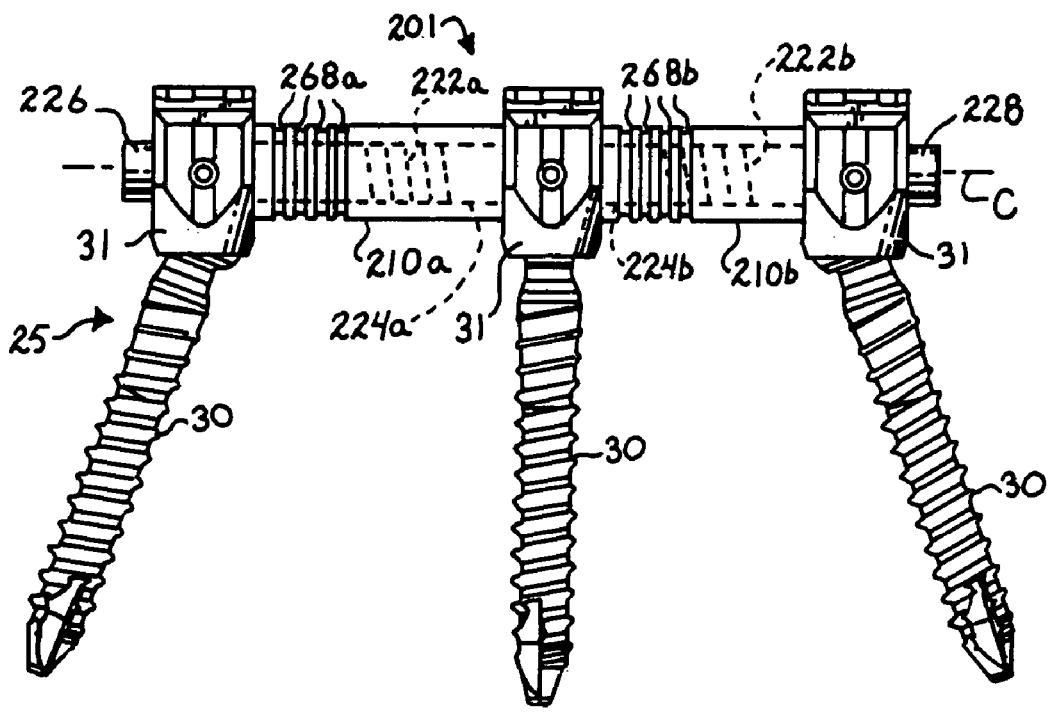
FIG. 13 is a front elevational view of a third longitudinal connecting member assembly according to the invention having the inner core of FIG. 12, a pair of outer sleeves cooperating with the pair of slitted portions and three bone screws.

With reference to FIGS. 12 and 13, another alternative longitudinal connecting member assembly according to the invention, generally 201 includes an inner core 208 and two outer sleeves 210a and 210b. The outer sleeves 210a and 210b are the same or substantially similar to the sleeve 10 previously described herein. The assembly 201 is shown attached to three bone screw assemblies 25, previously described herein, each bone screw assembly having a shank 30 and a receiver 31, also previously described herein. Although not shown, each bone screw assembly 25 further includes a closure structure 27, also previously described herein. As with the assemblies 1 and 101, the assembly 201 readily cooperates with a wide variety of bone anchors and closures, also as previously described herein.

The connecting member assembly 201 is sized and shaped to attach to at least three bone screw assemblies 25, to provide two flexible dynamic stabilization lengths or segments 224a and 224b where the core 108 has respective slits 222a and 222b that cooperate with the respective sleeves 210a and 210b. The core lengths or segments 224a and 224b and the slits 222a and 222b are similar or nearly identical to the core 8 and sleeve 10, respectively, previously described herein. The illustrated segment 224a is integral with the segment 224b. The flexible length 224a that includes the slit 222a is integral or otherwise fixed to a rigid length 226. The flexible length 224b that includes the slit 222b is integral or otherwise fixed to a rigid length 228. In the illustrated embodiment, the lengths 226 and 228 are relatively short in length, being sized and shaped to be received by a receiver 31 of one of the bone screw assemblies 25. The sleeves 210a and 210b each include respective grooves 268a and 268b that are the same or substantially similar to the grooves 68 previously described herein with respect to the sleeve 10. Also, in the illustrated embodiment, the portions 226 and 228 are substantially similar or identical to the end portions 16 and 18 previously described herein with respect to the core 8. It is noted that the portions 226 and 228 may also be elongate, similar to the length 126 of the core 108, for cooperating with more than one bone screw assembly 25.

Thus the assembly 201 according to the invention is used to provide protected movement of the spine along both the segments 224a and 225b. In the illustrated embodiment, the portions or segments 224a, 224b, 226 and 228 are integral and substantially uniform along a central longitudinal axis C thereof, and are cylindrical. The segments 224a, 224b, 226 and 228 are also of solid construction with the exception of the portions of the segments 224a and 224b that have the respective helical slits 222a and 222b. As indicated above, the helical slits 222a and 222b are substantially similar or identical to the helical slit 22 previously described herein, having features and cross-sections as shown in FIGS. 3, 4 and 5.

In use, the assembly 201 is implanted in a manner substantially similar to that previously described herein with respect to the assembly 1. As with the assembly 1, if desired, during tightening of the closure structures 27 against the core 208, one or both of the sleeves 210a and 210b may be compressed between facing bone screw receivers 31 as previously described herein with respect to the sleeve 10.

Figures 14, 15:
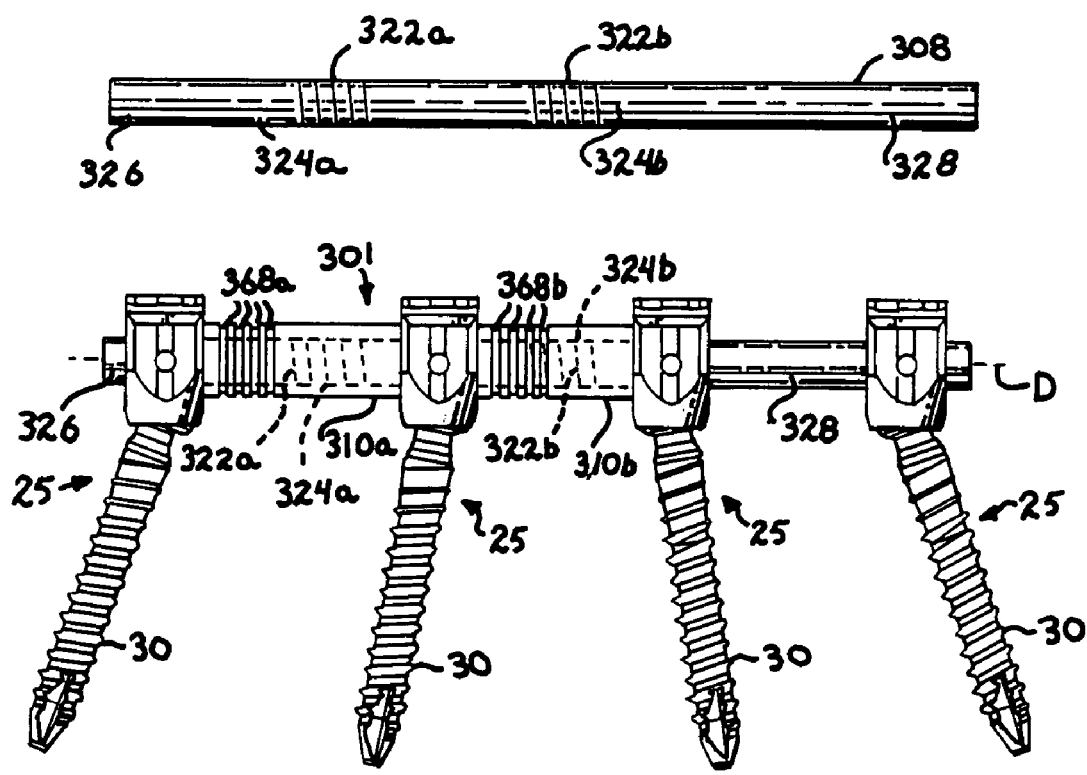
FIG. 14 is a front elevational view of a fourth embodiment of an inner core according to the invention having a pair of slitted portions and a solid portion.
FIG. 15 is a front elevational view of a fourth longitudinal connecting member assembly according to the invention having the inner core of FIG. 14, a pair of outer sleeves cooperating with the pair of slitted portions and four bone screws.

With reference to FIGS. 14 and 15, another alternative longitudinal connecting member assembly according to the invention, generally 301 includes an inner core 308 and two outer sleeves 310a and 310b. The outer sleeves 310a and 310b are the same or substantially similar to the sleeve 10 previously described herein. The assembly 301 is shown attached to four bone screw assemblies 25, previously described herein, each bone screw assembly having a shank 30 and a receiver 31, also previously described herein. Although not shown, each bone screw assembly 25 further includes a closure structure 27, also previously described herein. As with the assemblies 1, 101 and 201, the assembly 301 readily cooperates with a wide variety of bone anchors and closures, also as previously described herein.

The connecting member assembly 301 is sized and shaped to attach to at least four bone screw assemblies 25, to provide two flexible dynamic stabilization lengths or segments 324*a* and 324*b* and one rigid length 328. At the segments 324*a* and 324*b*, respective slits 322*a* and 322*b* cooperate with the respective sleeves 310*a* and 310*b*. The core lengths or segments 324*a* and 324*b* and the slits 322*a* and 322*b* are similar or nearly identical to the core 8 and sleeve 10, respectively, previously described herein. However, the segment 324*a* is integral with the segment 324*b* and the segment 324*b* is integral with the rigid length or segment 328. The flexible length 324*a* that includes the slit 322*a* is also integral or otherwise fixed to a shorter rigid length 326. In the illustrated embodiment, the length 326 is sized and shaped to be received by a receiver 31 of one of the bone screw assemblies 25 while the length 328 is elongate, of solid construction and sized to cooperate with at least two bone screw assemblies 25. The length 328 may be used in conjunction with spinal fusion. The sleeves 310*a* and 310*b* each include respective grooves 368*a* and 368*b* that are the same or substantially similar to the grooves 68 previously described herein with respect to the sleeve 10. Also, in the illustrated embodiment, the portion 326 is substantially similar or identical to the end portion 16 previously described herein with respect to the core 8. It is noted that the portion 326 may also be elongate, similar to the length 328, for cooperating with more than one bone screw assembly 25.

Thus the assembly 301 according to the invention is used to provide protected movement of the spine along both the segments 324*a* and 325*b* and rigid support along the length 328. In the illustrated embodiment, the portions or segments 324*a*, 324*b*, 326 and 328 are integral and substantially uniform along a central longitudinal axis D thereof, and are cylindrical. The segments 324*a*, 324*b*, 326 and 328 are also of solid construction with the exception of the portions of the segments 324*a* and 324*b* that have the respective helical slits 322*a* and 322*b*. As indicated above, the helical slits 322*a* and 322*b* are substantially similar or identical to the helical slit 22 previously described herein, having features and cross-sections as shown in FIGS. 3, 4 and 5.

In use, the assembly 301 is implanted in a manner substantially similar to that previously described herein with respect to the assembly 1. As with the assembly 1, if desired, during tightening of the closure structures 27 against the core 308, one or both of the sleeves 310*a* and 310*b* may be compressed between facing bone screw receivers 31 as previously described herein with respect to the sleeve 10.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least two bone attachment structures, including a first and a second bone attachment structure, the first and second bone attachment structures cooperating with a longitudinal connecting member, the improvement wherein the longitudinal connecting member comprises:
    a) an inner core having a periphery and a slit formed into a portion of the periphery, the core being integral along an entire length of the connecting member and secured to the first and second bone attachment structures; and
    b) an elastically compressible outer sleeve including opposed flat end surfaces adapted for flush engagement with a side surface of each of the first and second bone attachment structures, and covering the slit of the inner core, the sleeve disposed outside of the periphery, allowing respective freedom of movement between the inner core and the outer sleeve, the sleeve positioned entirely between the first and second bone attachment structures so as to be axially compressed by the first and second bone attachment structures, so as to provide a dynamic tension-compression relationship between the axially compressed sleeve and the inner core slitted portion.

2. The improvement of claim 1 wherein the slit is a helical slit disposed on a portion of the inner core and positioned between the first and second bone attachment structures.

3. The improvement of claim 1 wherein the sleeve extends between and makes contact with the first and second bone attachment structures, wherein the sleeve does not extend through the first and second bone attachment structures.

4. The improvement of claim 3 wherein the sleeve is compressed during installation.

5. The improvement of claim 1 wherein the core is cylindrical.

6. The improvement of claim 1 wherein the sleeve has an external surface with at least one groove formed in the surface.

7. The improvement of claim 1 wherin the sleeve has a cylindrical external surface with at least one and up to a plurality of compression grooves formed thereon.

8. The improvement of claim 1 wherein the inner core has a first longitudinal section and an integral second longitudinal section, the first longitudinal section having the slit, the first longitudinal section extending between the first and second bone attachment structures and the second longitudinal section extending between the second bone attachment structure and a third bone attachment structure.

9. The improvement of claim 8 wherein the second longitudinal section has a second slit.

10. The improvement of claim 8 wherein the second longitudinal section is a solid rod.

11. The improvement of claim 8 wherein the inner core member has a third longitudinal section extending between the third bone attachment structure and a fourth bone attachment structure.

12. In a medical implant assembly having at least first and second bone anchors cooperating with a longitudinal connecting member, the improvement wherein the connecting member comprises:
    a) an elongate bar of one-piece construction, the bar attachable to the first and second bone anchors, the bar having a slitted portion; and
    b) an elastically compressible outer sleeve including opposed flat end surfaces adapted for flush engagement with a side surface of each of the first and second bone attachment structures, and surrounding the slitted portion and being slidable with respect to the slitted portion, the sleeve being positioned entirely between the first and second bone anchors.

13. The improvement of claim 12 wherein the bar is substantially solid.

14. The improvement of claim 13 wherein the slitted portion is a substantially helical slit formed in the substantially solid bar.

15. The improvement of claim 12 wherein the bar is substantially cylindrical.

16. A longitudinal connecting member for cooperation with at least two bone anchors of a medical implant assembly, the assembly including a first bone anchor and a second bone anchor, the member comprising:
   a) a substantially solid bar of one-piece construction having first and second ends and a helical slit formed on a portion of the bar spaced from both the first and second ends; and
   b) a sleeve having a through bore, the bar receivable in the bore and freely slidable with respect to the sleeve, the sleeve being positioned over the bar portion having the helical slit, the sleeve being positioned entirely between and in contact with the first and second bone anchors, wherein the sleeve is elastically compressible and has initial flush engagement with at least one of the bone attachment structures when initially implanted.

* * * * *